United States Patent [19]

Leifeld

[11] Patent Number: 5,692,267
[45] Date of Patent: Dec. 2, 1997

[54] APPARATUS FOR RECOGNIZING IMPURITIES OF FIBER MATERIAL DURING PROCESSING IN A TEXTILE MACHINE AND METHOD

[75] Inventor: Ferdinand Leifeld, Kempen, Germany

[73] Assignee: Trützschler GmbH & Co. KG, Möchengladbach, Germany

[21] Appl. No.: 627,068

[22] Filed: Apr. 3, 1996

[30] Foreign Application Priority Data

Apr. 13, 1995 [DE] Germany ................... 195 14 038.9
Feb. 8, 1996 [DE] Germany ................... 196 04 499.5

[51] Int. Cl.$^6$ .................................................. D01G 15/46
[52] U.S. Cl. .................. 19/106 R; 19/296; 19/161.1; 356/237
[58] Field of Search .................. 19/106 R, 0.21, 19/0.23, 66 R, 200, 203, 98, 99, 288, 65 A, 150, 296, 300, 161.1; 356/237, 238, 335

[56] References Cited

U.S. PATENT DOCUMENTS

| 4,271,565 | 6/1981 | Grunder ................... 19/106 R |
| 4,272,868 | 6/1981 | Grunder et al. .......... 19/106 R |
| 4,953,265 | 9/1990 | Scheinhütte . |
| 5,123,144 | 6/1992 | Demuth et al. .......... 19/65 A |
| 5,130,559 | 7/1992 | Leifeld et al. . |
| 5,173,995 | 12/1992 | Pezzoli et al. .......... 19/0.21 |
| 5,270,787 | 12/1993 | Shofner et al. .......... 356/238 |
| 5,321,496 | 6/1994 | Shofner et al. .......... 356/238 |
| 5,345,515 | 9/1994 | Nishi et al. .......... 356/238 |
| 5,410,401 | 4/1995 | Shofner et al. .......... 356/238 |

FOREIGN PATENT DOCUMENTS

| 0 331 039 | 9/1989 | European Pat. Off. . |
| 0 399 945 | 11/1990 | European Pat. Off. . |
| 0 562 268 | 9/1993 | European Pat. Off. . |
| 0 604 875 | 7/1994 | European Pat. Off. . |
| 37 34 145 | 4/1989 | Germany . |
| 39 26 346 | 2/1991 | Germany . |
| 39 28 279 | 2/1991 | Germany . |
| 40 18 847 | 12/1991 | Germany . |
| 5-25713 | 2/1993 | Japan . |
| 6-81224 | 3/1994 | Japan . |
| 2 210 907 | 1/1989 | United Kingdom . |
| 2 225 634 | 6/1990 | United Kingdom . |
| 2 236 389 | 4/1991 | United Kingdom . |
| 93/19359 | 9/1993 | WIPO ................... 356/238 |
| 95/22762 | 8/1995 | WIPO . |

*Primary Examiner*—Michael A. Neas
*Attorney, Agent, or Firm*—Spencer & Frank

[57] ABSTRACT

A fiber processing apparatus includes a plurality of serially-arranged fiber processing components for forming and advancing a fiber web and for gathering the web into a sliver. Some of the components are spaced by a clearance from one another such that the fiber web, while passing from one of the components to an adjoining, spaced component has a length portion unsupported by either of the adjoining components. There are further provided an imaging apparatus which has an illuminating device directing a light beam onto a surface area of the unsupported length portion of the running web; and a camera for sensing the light of the surface area lit by the illuminating device. An electronic image processing unit is connected to the camera for examining signals received therefrom.

24 Claims, 6 Drawing Sheets

APPARATUS FOR RECOGNIZING IMPURITIES OF FIBER MATERIAL DURING PROCESSING IN A TEXTILE MACHINE AND METHOD

CROSS REFERENCE TO RELATED APPLICATION

This application claims the priority of German Application Nos. 195 14 038.9 filed Apr. 13, 1995 and 196 04 499.5 filed Feb. 8, 1996.

BACKGROUND OF THE INVENTION

This invention relates to an apparatus associated with a carding machine, for recognizing foreign bodies, particularly trash particles, neps, seed coat fragments and the like in a textile material such as cotton or chemical fibers. The apparatus includes a camera, such as a diode-line camera for determining the degree of soiling along a measuring path between the doffer-stripping roll and the crushing roll pair of the card, an illuminating device for illuminating the running fiber material along the measuring path and an electronic evaluating device (image processing unit).

SUMMARY OF THE INVENTION

It is an object of the invention to provide an improved apparatus of the above-outlined type in which the evaluation of the measuring results is ameliorated.

This object and others to become apparent as the specification progresses, are accomplished by the invention, according to which, briefly stated, the fiber processing apparatus includes a plurality of serially-arranged fiber processing components for forming and advancing a fiber web and for gathering the web into a sliver. Some of the components are spaced by a clearance from one another such that the fiber web, while passing from one of the components to an adjoining, spaced component has a length portion unsupported by either of the adjoining components. There are further provided an imaging apparatus which has an illuminating device directing a light beam onto a surface area of the unsupported length portion of the running web, and a camera for sensing the light of the surface area lit by the illuminating device. An electronic image processing unit is connected to the camera for examining signals received therefrom.

By virtue of the fact that the camera is associated with a running web portion which is in a transitional zone between fiber processing components, that is, the web portion is not supported (backed up) by such fiber processing components, an image formation of the particles is possible without interference by the clothing or other fiber-treating surface of the components. In this manner, the evaluation of the measuring results is concentrated on the particles present in the web and detected by the apparatus so that an overall substantially improved recognition of the interfering particles in the fiber web is achieved.

DESCRIPTION OF THE PREFERRED EMBODIMENTS

Figure 1:
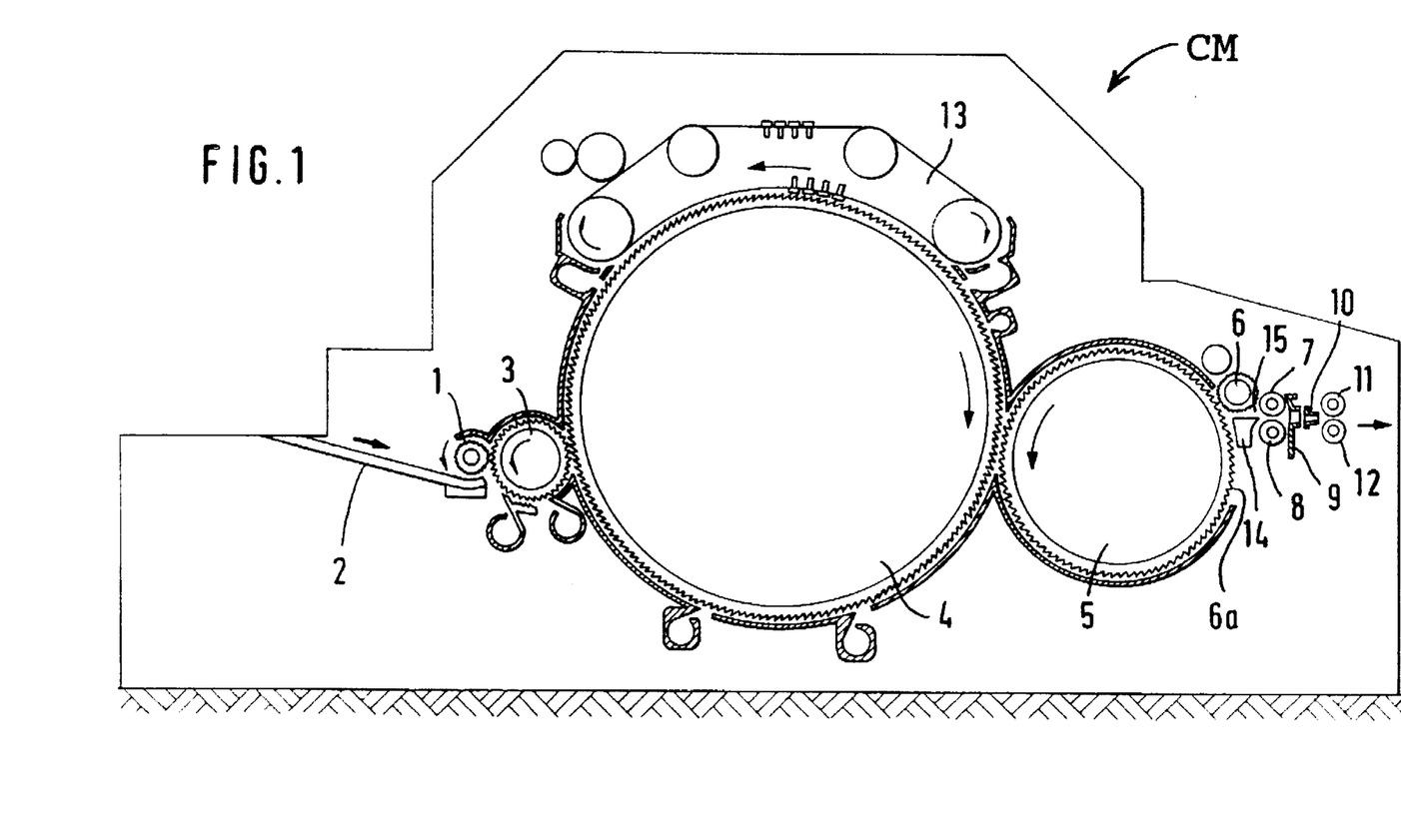
FIG. 1 is a schematic side elevational view of a carding machine including a web supporting and guiding body accommodating the apparatus according to the invention.

FIG. 1 illustrates a carding machine CM which may be, for example, an EXACTACARD DK 760 model manufactured by Trützschler GmbH & Co. KG, Mönchengladbach, Germany. The carding machine CM has a feed roll 1, a feed table 2 cooperating with the feed roll 1, a licker-in 3, a main carding cylinder 4, a doffer 5, a stripping roll 6, cooperating crushing rolls 7, 8, a web guiding element 9, a sliver trumpet 10, cooperating calender rolls 11, 12 and travelling flats 13. Underneath the stripping roll 6 a web supporting and guiding body 14 is arranged. The upper crushing roll 7 is situated in a close vicinity of the stripping roll 6. The direction of rotation of the main carding cylinder and the other rolls is illustrated by respective curved arrows.

Figure 2:
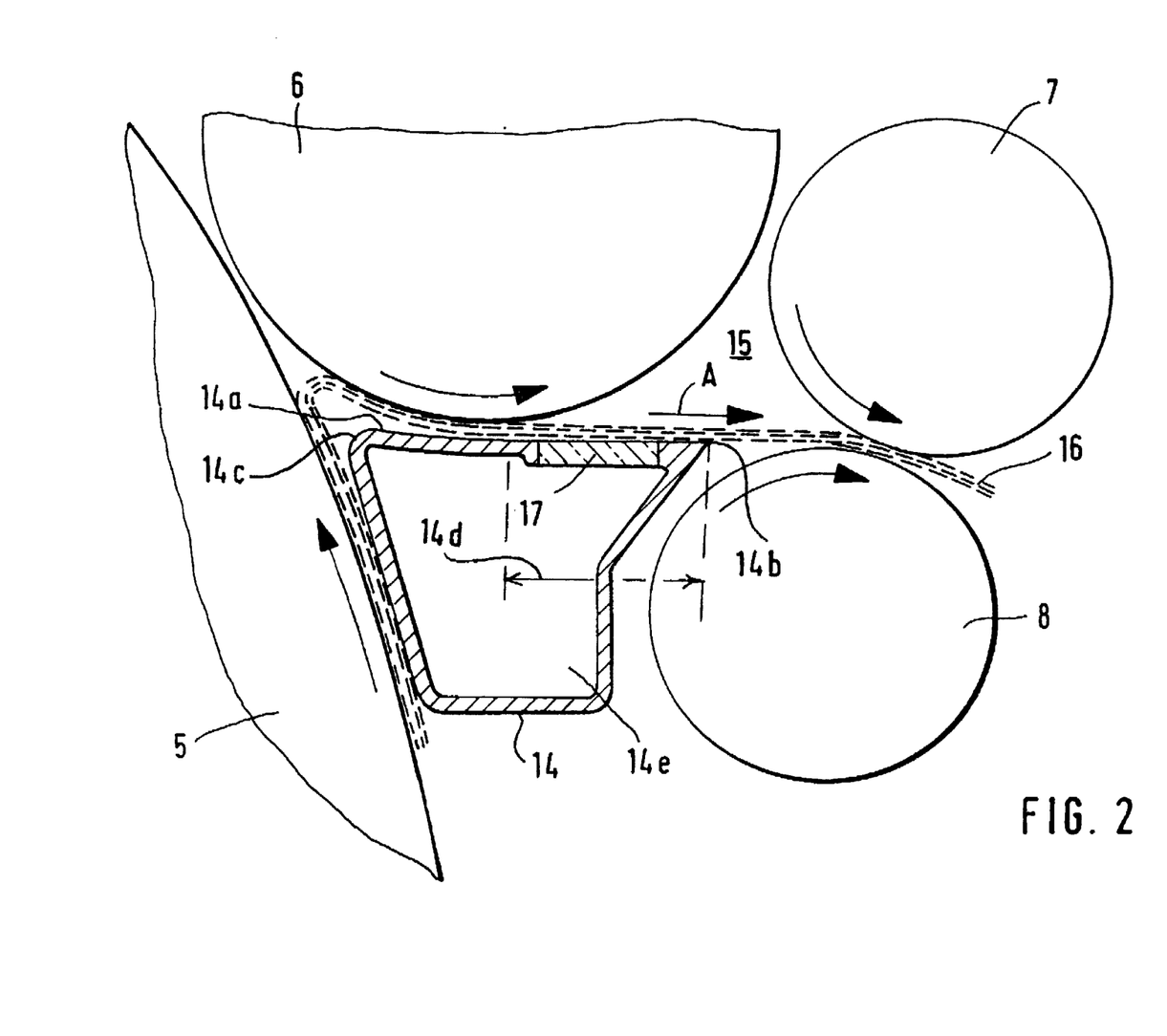
FIG. 2 is a schematic sectional side elevational view of an enlarged detail of FIG. 1.

FIG. 2 illustrates the part of the carding machine which contains the doffer 5, the stripping roll 6 and the crushing rolls 7 and 8. In the region 15 the fiber web 16 passes from the stripping roll 6 to the cooperating crushing rolls 7, 8 in the running direction A. For supporting and guiding the fiber web 16 in the region 15 where the fiber web 16 is not backed up by any rolls, the supporting and guiding body 14 is provided which has a generally rectangular cross-sectional outline and which extends substantially over the entire axial length of the stripping roll 6. The body 14 is expediently an extruded member made of aluminum having a hollow inner space 14e. The upper surface 14a of the body 14 is of a slightly concave configuration, whose radius of curvature is greater than the radius of the stripping roll 6. The frontal edge 14b is sharp whereas the rear edge 14c is rounded. The angular edge 14b prevents the deposition of impurities, such as honeydew. The contacting sliding region 14d of the surface 14a is continuously cleaned of impurities, such as trash, by the web 16 sliding thereon. The cross-sectional configuration of the body 14 is adapted to the air flow conditions in the region between the doffer 5, the stripping roll 6 and the crushing rolls 7, 8. The end region 14b serves as a support and a guide for the web 16 just prior to its passage into the nip of the cooperating crushing rolls 7, 8. The end regions 14b and 14c of the body 14 are situated on different sides of a vertical axial plane of the stripping roll 6. The body 14, in addition to its web supporting and guiding role, also functions as a housing, as will be described in more detail later (the body 14 is therefore also referred to as housing). In the contact zone 14d the housing 14 has a light-transparent window 17 which extends substantially along the entire axial length of the stripping roll 6. The web 16 is, as may be best observed in FIG. 2, taken over from the doffer 5 by the clothing 6a (FIG. 1) of the stripping roll 6 and is removed from the stripping roll 6 slightly after passing the vertical axial plane thereof and is guided on the surface 14a of the body 14 in the direction A. After leaving the edge 14b of the body 14, the web 16 is unsupported and enters the nip formed between the crushing rolls 7 and 8 and passes therethrough. The upper surface 14a of the body 14 is oriented towards the clothing 6a of the stripping roll 6. The rounded edge 14c of the body 14 is oriented towards the gap formed between the doffer 5 and the stripping roll 6. The edge 14b is oriented towards the nip defined between the crushing rolls 7 and 8.

Figure 3:
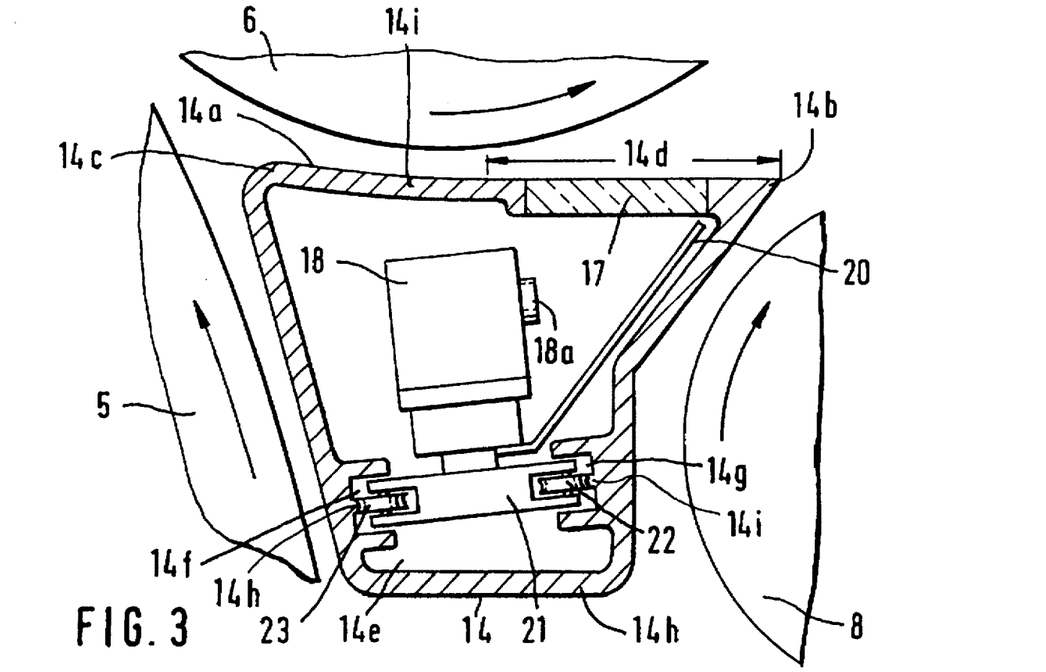
FIG. 3 is a schematic sectional elevational view, similar to FIG. 2, illustrating the installed apparatus according to the invention.

As shown in FIG. 3, in the chamber 14e of the body 14 a carriage 21 is disposed, carrying a camera 18, for example a diode-line camera, an illuminating device 19 which may be formed, for example, of several light diodes and a deflecting mirror 20. The mirror 20 is oriented at such an angle so as to provide a line of sight for the objective 18a of the camera 18 and the illuminating device 19 to the web 16 which runs on the outer face of the window 17.

The carriage 21 has three guide wheels 22, 23 and 24. The guide wheel 22 runs on a rail 14i extending in a trough 14g longitudinally of the housing 14, while the guide wheels 23 and 24 which are arranged on a side of the carriage 21 opposite the guide wheel 22, run on a rail 14h extending in a trough 14f longitudinally of the housing 14.

Figure 4:
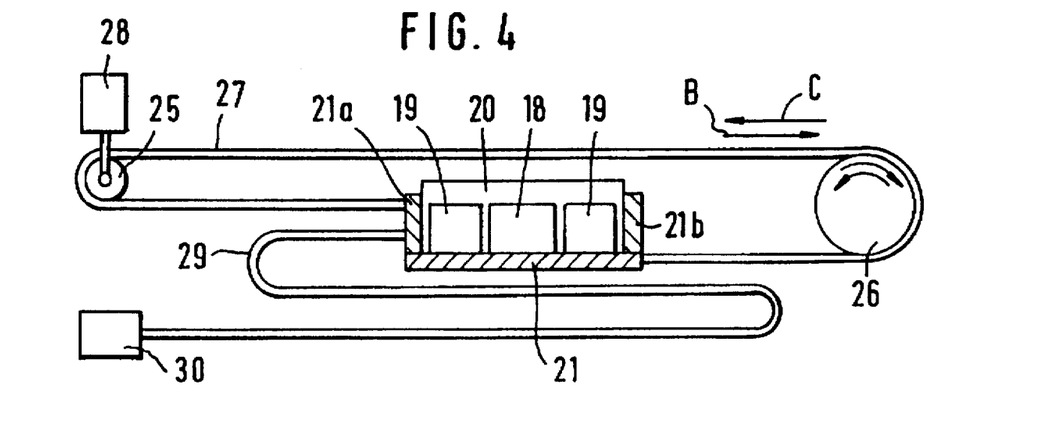
FIG. 4 is a schematic side elevational view illustrating a mechanical cable drive and electric conductors for the apparatus according to the invention.
Figure 5:
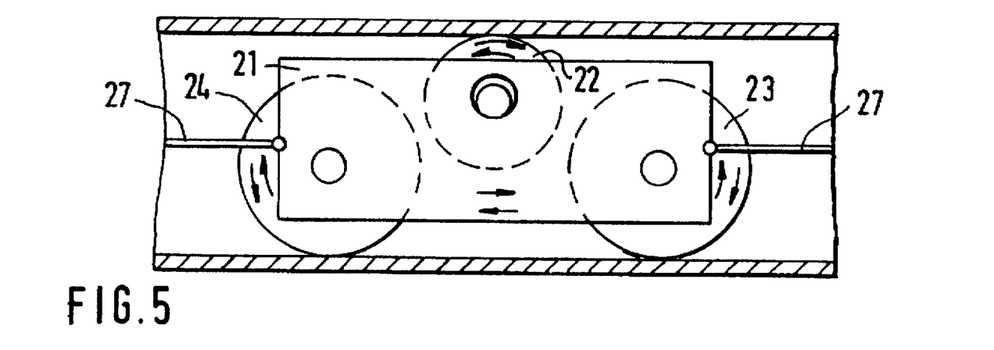
FIG. 5 is a schematic sectional top plan view of a camera-displacing carriage and its support.

With particular reference to FIG. 4, the two ends of a pull cable 27 are attached to respective opposite end faces 21a, 21b of the carriage 21. At opposite ends of the housing 14 the cable 27 is supported by end rollers 25 and 26. A motor 28 drives the roller 25 to thus displace the carriage 21 in the direction B or C. Electric conductors, preferably combined into a flexible flat cable 29, connect the camera 18 and the illuminating devices 19 with an electronic control and regulating device such as a microcomputer 30.

Figure 6:
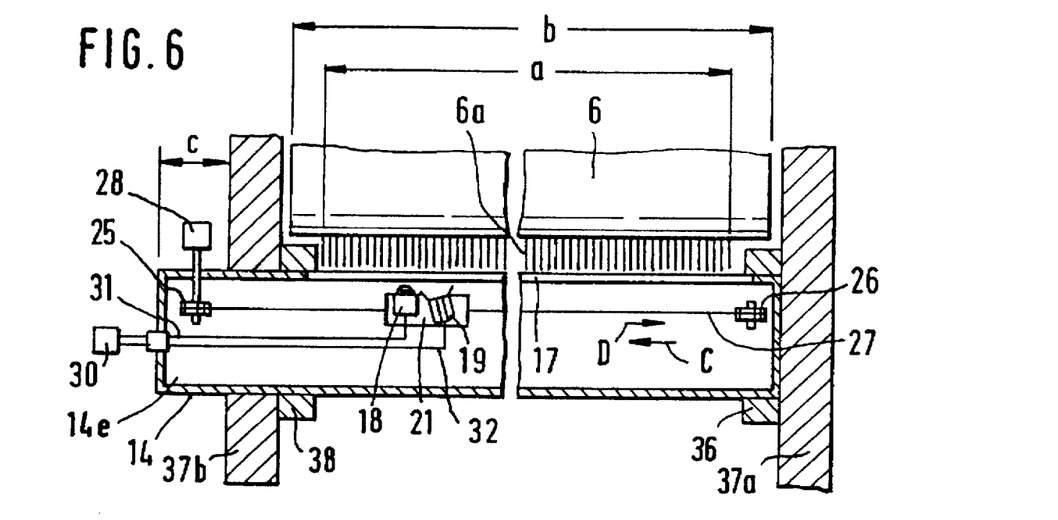
FIG. 6 is a schematic sectional front elevational view of another embodiment according to the invention.

In the embodiment illustrated in FIG. 6, one end of the housing 14 may be inserted into a socket 36 which is affixed to the carding frame 37a and whose receiving space is complemental with the peripheral outline of the housing 14 to provide for a form-fitting engagement between the components 14 and 36. When in the installed position as illustrated in FIG. 6, the outer end face of the housing 14 is in a face-to-face engagement with the inner surface of the frame 37a. The other end region of the housing 14 passes through aligned apertures provided in a guide bracket 38 and the frame portion 37b of the carding machine. At this end too, the housing 14 is form-fittingly supported and is thus firmly positioned in the carding frame during operation. The housing 14 may further be secured by screws (not shown) against displacement. One end of the housing 14 projects beyond the frame 37b by a distance c, whereby a grip is provided for facilitating replacement. The two cable pulleys 25 and 26 supporting the cable 27 are positioned inside the housing 14. The camera 18 and the illuminating device 19 mounted on the carriage 21 are oriented toward the window 17 and thus a light-deflecting mirror as described in connection with FIG. 3 is not needed. The camera 18 and the illuminating device 19 are connected with respective conductors 31 and 32 to the control and regulating device 30. The axial length of the stripping roll 6 is designated at b whereas the axial length of the clothing 6a is designated a.

Figure 7:
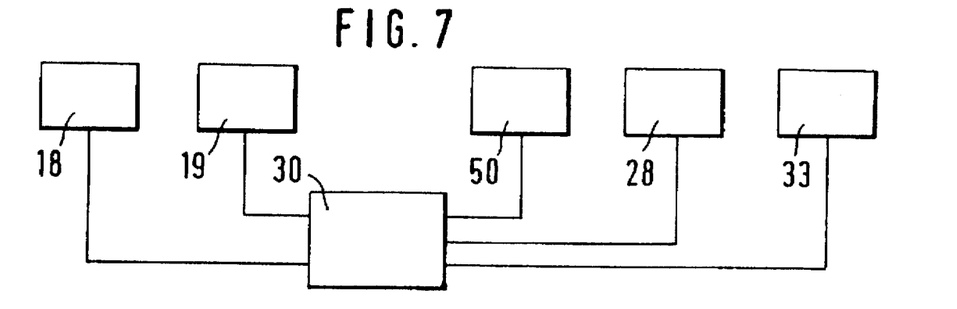
FIG. 7 is a block diagram for the control of the apparatus according to the invention.

As shown in FIG. 7, the camera 18, the illuminating device 19, an image evaluating device 50, the electric motor 28 and a device 33 measuring the rpm of the stripping roll 6 are connected to the control and regulating device 30.

Figure 8:
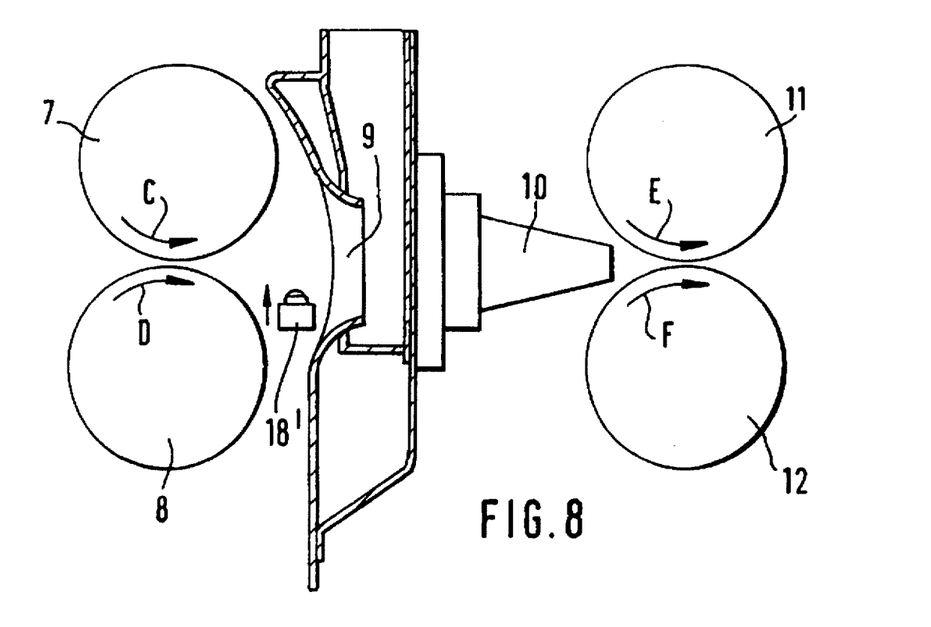
FIG. 8 is a schematic side elevational view illustrating an arrangement of the apparatus according to the invention between the crushing roll pair and a web guiding (web gathering) device of the carding machine.
Figure 9:
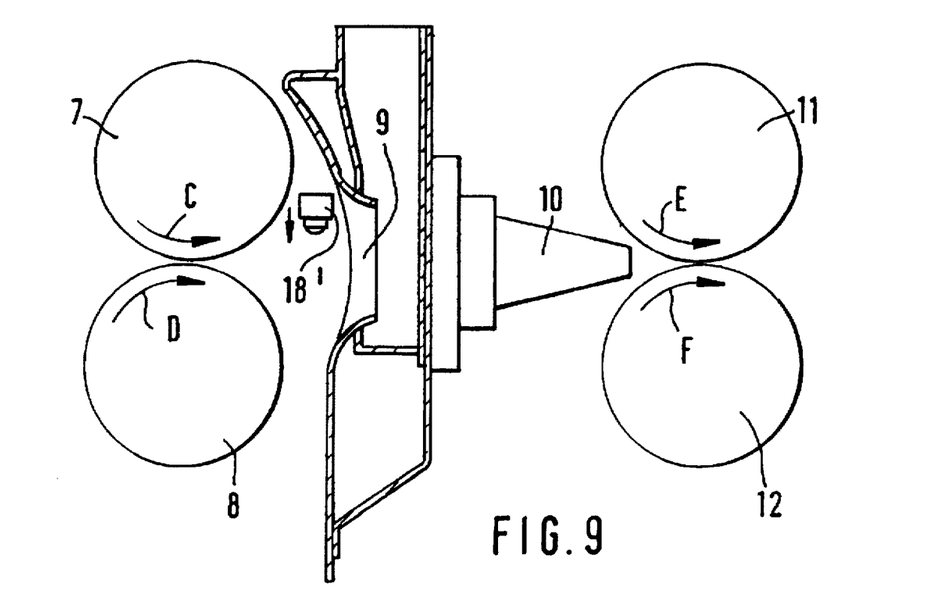
FIG. 9 is a view similar to FIG. 8, illustrating the arrangement of the camera in an orientation opposite to that shown in FIG. 8.

Turning to FIG. 8, between the crushing rolls 7, 8 and the calender rolls 11, 12 a web guiding device 9 is arranged which may be a WEBSPEED model, manufactured by Trützschler GmbH & Co. KG, Mönchengladbach, Germany. After being discharged by the nip defined between the crushing rolls 7 and 8 along the entire width of the carding machine, the web 16 is gathered by the web guiding device 9 and is passed through an opening of the device 9. Thereafter the gathered web is introduced into a trumpet 10 which forms the fiber sliver. A camera 18' is situated underneath the plane which passes through the nip of the crushing rolls 7 and 8 and the approximate middle of the opening in the web guiding device 9. Thus, during operation, the camera 18' is situated underneath the running fiber web 16 and the camera objective is oriented upwardly. As shown in FIG. 9, it is also feasible to provide the camera 18' above such plane in which case the camera 18' is situated above the running fiber web 16 and is oriented downwardly.

Figure 10:
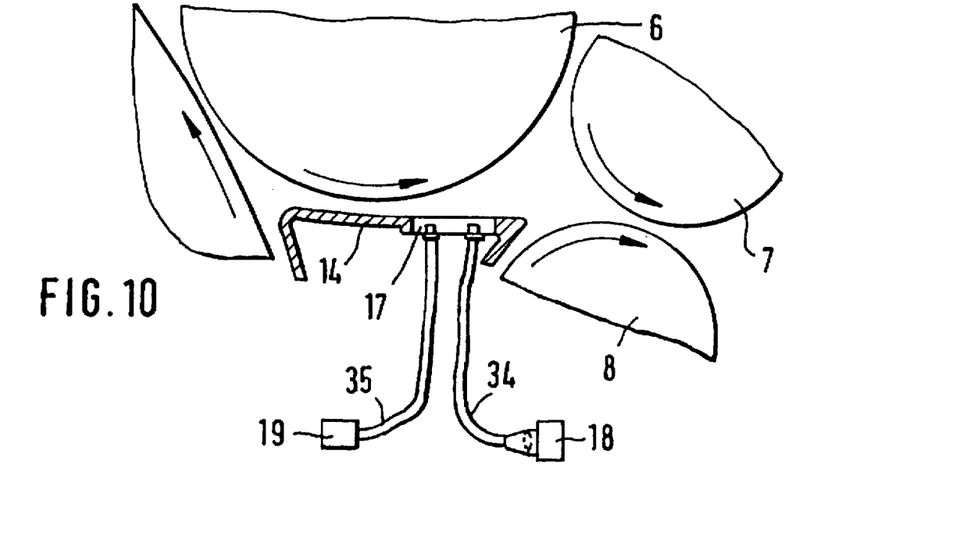
FIG. 10 is a schematic sectional side elevational view of the doffer area of the carding machine illustrating the use of optical wave guides for the apparatus according to the invention.

In the embodiment according to FIG. 10, the camera 18 and the illuminating device 19 are stationarily supported, for example, externally of the carding machine. The objective of the camera 18 and the light emitting element of the illuminating device 19 are connected with an end of respective optical wave guides (such as optical fiber cables) 34, 35, whose respective other end is supported in the web supporting and guiding body 14 in an orientation toward the light-transparent window 17. The optical wave guides 34, 35 may be moved along the axial length of stripping roller 6 by means of a carriage assembly as described earlier in connection with FIG. 6. The embodiment of FIG. 10 is advantageous in that the spatial requirement for the travelling components, namely, the end portion of the respective optical wave guides 34 and 35 is substantially less than in case of other embodiments where the camera and the illuminating device proper are to be displaced.

Figure 11:
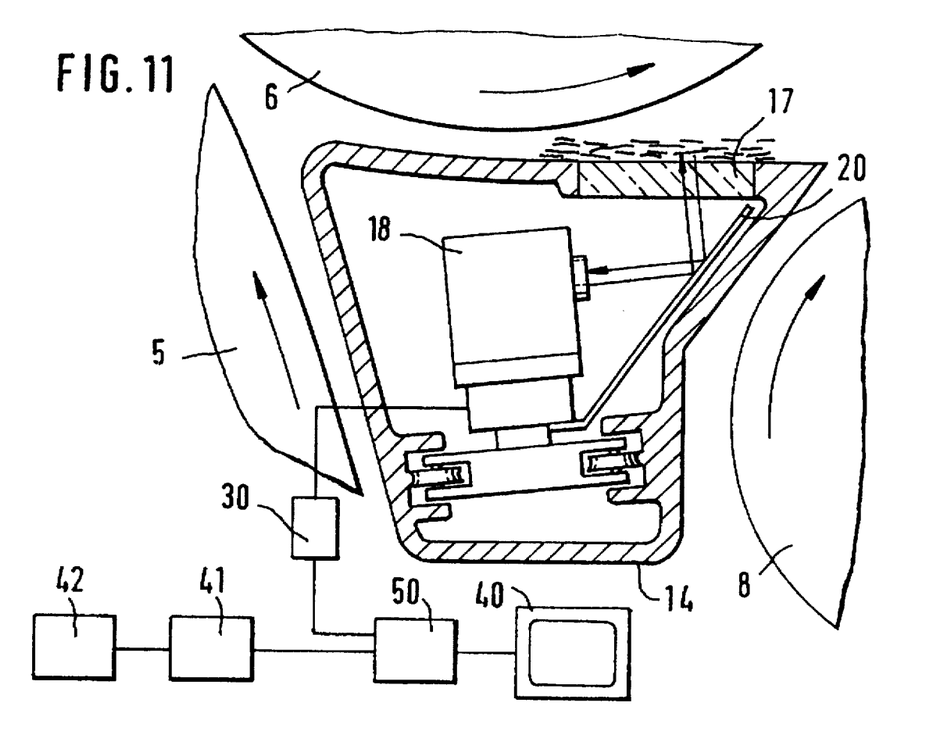
FIG. 11 is a view similar to FIG. 3, further illustrating a block diagram for the evaluation of data supplied by the apparatus according to the invention.

Turning to FIG. 11, the apparatus according to the invention makes possible an on-line nep count instead of taking random samples under laboratory testing conditions. The device utilized with the apparatus according to the invention, may be, for example, a NEPCONTROL NCT-model manufactured by Trützschler GmbH & Co. KG which is an on-line measuring system to recognize trash, seed coat fragments and neps. In the region of the web doffing underneath the stripping roll 6, the video camera 18 reciprocates within the web supporting and guiding body 14 parallel to the working width of the carding machine. The camera 18 delivers, even at an output speed of 300 m/min, sharp images of the web 16 and transmits the signals representing the images to the computer 30 of the NEPCONTROL NCT. The latter evaluates the images according to number, type and size of the interfering particles. Such an evaluation is able to distinguish between trash particles and seed coat fragments or neps. The results are shown in a display device 40 via a machine control 49 which may be a CARD-COMMANDER model manufactured by Trützschler GmbH & Co. KG. Or, the results may be transmitted to a non-illustrated sliver information system which may be a KIT model by Trützschler GmbH & Co. KG.

The apparatus according to the invention is easy to install or remove from a carding machine, whereby a periodic measurement on different carding machines is feasible.

The illumination may be effected by incident light as shown in FIG. 11, combined with strobolights. The evaluation is performed according to the principle of actual and desired value comparisons. As a desired parameter the reflection intensity in relation to the incident beam intensity is utilized. The characteristic of the inputted fiber material (such as cotton) is automatically determined by the system and utilized as a reference value. Materials with different characteristics are recognized if the dimension is, for example, 5 mm in the direction of the smallest axis.

A reflecting light module may comprise a semiconductor flash unit with high homogeneity, a command-controlled, high-speed measuring camera 18 with a digital data output as disclosed, for example, in German Offenlegungsschrift 43 13 621 and a deflecting mirror 20 for reducing the structural height. A transmitting light module may comprises a large-area semiconductor flashlight illumination with high intensity.

In operation, transmitted light or reflected light may be utilized for recognizing neps and foreign particles. Two pictures are taken in a very rapid succession, once with transmitted light and once with reflected light. Both images are combined and evaluated together. The light is flashed on command by the camera 18 or its control. For the individual takes, light of different wavelengths may be used. It is feasible to utilize more than one illuminating device for taking a picture. For example, the reflecting light module may have a plurality of illuminating devices. Illumination may occur from different directions. Also, the illumination may be effective from different sides (transmitted light or reflected light). For the illumination light sources with different wavelengths may be used. Also, the different directions, sides or wavelengths may be combined with one another. Further, different exposure times may be utilized.

Reverting to FIG. 11, the camera 18 and the illuminating devices (not shown in FIG. 11) are connected with the intermediary of the computer 30 with the image processing device 50 to which a monitor 40, a control element 41 (for example, the machine control) and a setting device 42 for affecting the number of neps, trash particles and/or seed coat fragments in the web are connected. The device 42 may trigger measures to change the number of the neps in the web for example, by changing the distance between the flats clothing and the cylinder clothing of the carding machine, or the rpm of the cylinder 4, or the distance between a mote knife and a roller associated therewith or a guide element or the like.

The apparatus according to the invention makes possible an automatic detection and reduction of the number of neps in the fiber web. The detection at the fiber web is of importance at a location where it has already been removed from the stripping roll 6.

The invention has been described in connection with a carding machine; it will be understood that it may find application in other web producing machines such as a roller card unit.

It will be understood that the above description of the present invention is susceptible to various modifications, changes and adaptations, and the same are intended to be comprehended within the meaning and range of equivalents of the appended claims.

What is claimed is:

1. A fiber processing apparatus comprising
(a) a plurality of serially-arranged fiber processing components for forming and advancing a fiber web and for gathering the web into a sliver; some of said components being adjoining components spaced from one another such that the fiber web, while passing from one of said components to an adjoining, spaced component has a length portion unsupported by either of the adjoining components; and
(b) an imaging apparatus including
(1) an illuminating device directing a light beam onto a surface area of said length portion of the running web; said illuminating device being stationarily supported remotely from the running web;
(2) a camera for sensing the light of the surface area lit by said illuminating device; said camera being stationarily supported remotely from the running web; and
(3) an electronic image processing unit connected to said camera for examining signals received therefrom; and
(c) an optical wave guide having first ends being adjacent to and in a line of sight of said length portion of said running web; said optical wave guide having second ends being connected to said illuminating device and said camera.

2. A fiber processing apparatus comprising
(a) a plurality of serially-arranged fiber processing components for forming and advancing a fiber web and for gathering the web into a sliver; some of said components being adjoining components spaced from one another such that the fiber web, while passing from one of said components to an adjoining, spaced component has a length portion unsupported by either of the adjoining components; said components including a doffer, a stripping roll and two crushing rolls; said crushing rolls together defining a nip through which the fiber web passes; said length portion of said fiber web extending between said stripping roll and said nip;
(b) an imaging apparatus including
(1) an illuminating device directing a light beam onto a surface area of said length portion of the running web;
(2) a camera for sensing the light of the surface area lit by said illuminating device; and
(3) an electronic image processing unit connected to said camera for examining signals received therefrom;
(c) a hollow, web supporting and guiding body positioned in a space defined together by said doffer, said stripping roll and said crushing rolls; said web supporting and guiding body extending along an axial length of said doffer, said stripping roll and said crushing rolls; said web supporting and guiding body having a wall oriented towards said doffer and extending toward said nip defined between said crushing rolls; said wall having an upper surface for supporting and guiding the running fiber web during passage thereof from said doffer towards said nip; said web supporting and guiding body constituting a housing accommodating said illuminating device and said camera.

3. The fiber processing apparatus as defined in claim 2, further comprising a carriage supporting said camera and said illuminating device and guide means for guiding said carriage for motion along a length of said web supporting and guiding body.

4. The fiber processing apparatus as defined in claim 3, wherein said guide means comprises runner wheels mounted on said carriage and rails held within said web supporting and guiding body and extending parallel to the length thereof; said wheels running on said rails.

5. The fiber processing apparatus as defined in claim 3, wherein said guide means comprises two end rollers supported in said web supporting and guiding body at opposite ends thereof; a pull cable attached to said carriage and a motor driving one of said end rollers for displacing said carriage by said pull cable.

6. The fiber processing apparatus as defined in claim 2, further including a machine frame and further wherein said web supporting and guiding body is stationarily supported in said machine frame.

7. The fiber processing apparatus as defined in claim 6, wherein said machine frame comprises first and second frame members situated adjacent opposite longitudinal ends of said doffer, said stripping roll and said crushing rolls; further comprising a socket affixed to said first frame member and receiving an end of said web supporting and guiding body and an aperture provided in said second frame member; said web supporting and guiding body passing through said aperture.

8. The fiber processing apparatus as defined in claim 7, wherein said aperture is in alignment with said socket, whereby said web supporting and guiding body is introducible through said aperture and, by sliding therethrough, receivable in said socket.

9. The fiber processing apparatus as defined in claim 8, wherein said socket and said aperture are complemental to a peripheral outline of said web supporting and guiding body, whereby said body is form-fittingly received in said socket and in said aperture.

10. The fiber processing apparatus as defined in claim 2, wherein said wall includes a light-transparent window for maintaining a line of sight for said illuminating device and said camera toward the running web sliding on said surface.

11. The fiber processing apparatus as defined in claim 10, further comprising a mirror mounted on said carriage and being oriented such as to provide a line of sight through said window for said illuminating device and said camera toward the running fiber web.

12. The fiber processing apparatus as defined in claim 10, wherein said camera and said illuminating device are oriented such as to be in a direct line of sight with the running web through said web supporting and guiding body.

13. A fiber processing apparatus comprising
  (a) a plurality of serially-arranged fiber processing components for forming and advancing a fiber web and for gathering the web into a sliver; said plurality of serially-arranged fiber processing components including first and second serially-arranged adjoining fiber processing components spaced from one another by a clearance such that the fiber web, while passing from the first component to the second component has a length portion unsupported by either of the first and second components;
  (b) an imaging apparatus including
    (1) an illuminating device directing a light beam onto a surface area of said length portion of the running web;
    (2) a camera for sensing the light of the surface area lit by said illuminating device; and
    (3) an electronic image processing unit connected to said camera for examining signals received therefrom; and
  (c) a hollow, web supporting and guiding body positioned in said clearance; said web supporting and guiding body extending along an axial length of said first and second components; said web supporting and guiding body constituting a housing accommodating said camera; said web supporting and guiding body including a wall having an upper surface for supporting and guiding the running fiber web during passage thereof from said first component to said second component.

14. The fiber processing apparatus as defined in claim 13, further comprising a carriage supporting said camera and guide means for guiding said carriage for motion along a length of said web supporting and guiding body.

15. The fiber processing apparatus as defined in claim 14, wherein said guide means comprises runner wheels mounted on said carriage and rails held within said web supporting and guiding body and extending parallel to the length thereof; said wheels running on said rails.

16. The fiber processing apparatus as defined in claim 14, wherein said guide means comprises two end rollers supported in said web supporting and guiding body at opposite ends thereof; a pull cable attached to said carriage and a motor driving one of said end rollers for displacing said carriage by said pull cable.

17. The fiber processing apparatus as defined in claim 13, wherein said illuminating device is accommodated in said web supporting and guiding body; further wherein said wall includes a light-transparent window for maintaining a line of sight for said illuminating device and said camera toward the running web sliding on said surface.

18. The fiber processing apparatus as defined in claim 17, further comprising a mirror mounted on said carriage and being oriented such as to provide a line of sight through said window for said illuminating device and said camera toward the running fiber web.

19. The fiber processing apparatus as defined in claim 13, wherein said camera is a diode-line camera.

20. A fiber processing apparatus as defined in claim 13, wherein said components include two crushing rolls together defining a nip through which the fiber web passes and a web guiding element spaced from said nip and arranged for gathering the fiber web; said web guiding element having an aperture through which the gathered fiber web passes; said length portion of said fiber web extending between said nip and said aperture.

21. A fiber processing apparatus comprising
  (a) a plurality of serially-arranged fiber processing components for forming and advancing a fiber web and for gathering the web into a sliver; some of said components being adjoining components spaced from one another such that the fiber web, while passing from one of said components to an adjoining, spaced component has a length portion unsupported by either of the adjoining components; and
  (b) an imaging apparatus including
    (1) an illuminating device directing a light beam onto a surface area of said length portion of the running web;
    (2) a camera for sensing the light of the surface area lit by said illuminating device; and
    (3) an electronic image processing unit connected to said camera for examining signals received therefrom;
  (c) a drive motor for moving parts of said imaging apparatus parallel to a width of the fiber processing apparatus; and
  (d) an electronic control and regulating device; said illuminating device, said camera, said electronic image processing unit and said drive motor being connected to said electronic control and regulating device.

22. The fiber processing apparatus as defined in claim 21, further comprising a setting device for regulating a degree of cleaning the fiber material; said setting device being connected to said electronic control and regulating device.

23. The fiber processing apparatus as defined in claim 22, further comprising a carding cylinder, a control element and a setting element; said control element and said setting element being connected to said electronic control and regulating device for controlling an rpm of said carding cylinder.

24. The fiber processing apparatus as defined in claim 22, further comprising a carding cylinder having a clothing, travelling flats including flat bars having a clothing, a control element and a setting element; said control element and said setting element being connected to said electronic control and regulating device for controlling a distance between said clothing of said carding cylinder and the clothing of said flat bars.

* * * * *